United States Patent
Bansal

(10) Patent No.: US 12,109,240 B2
(45) Date of Patent: Oct. 8, 2024

(54) SYNERGISTIC COMPOSITION WITH ANTI-PROLIFERATIVE ACTIVITY

(71) Applicant: SHASHVI REMEDIES (OPC) PRIVATE LIMITED, Navi Mumbai-Raigad Maharashtra (IN)

(72) Inventor: Ashvany Kumar Bansal, Navi Mumbai-Raigad Maharashtra (IN)

(73) Assignee: SHASHVI REMEDIES (OPC) PRIVATE LIMITED, Navi Mumbai-Raigad Maharashtra (IN)

( * ) Notice: Subject to any disclaimer, the term of this patent is extended or adjusted under 35 U.S.C. 154(b) by 635 days.

(21) Appl. No.: 17/430,829

(22) PCT Filed: Feb. 12, 2020

(86) PCT No.: PCT/IB2020/051111
§ 371 (c)(1),
(2) Date: Aug. 13, 2021

(87) PCT Pub. No.: WO2020/165779
PCT Pub. Date: Aug. 20, 2020

(65) Prior Publication Data
US 2022/0160775 A1 May 26, 2022

(30) Foreign Application Priority Data
Feb. 15, 2019 (IN) .............................. 201921006145

(51) Int. Cl.
*A61K 36/00* (2006.01)
*A61K 35/22* (2015.01)
*A61K 36/9066* (2006.01)

(52) U.S. Cl.
CPC .......... *A61K 35/22* (2013.01); *A61K 36/9066* (2013.01)

(58) Field of Classification Search
CPC ................................................. A61K 36/9066
See application file for complete search history.

(56) References Cited

U.S. PATENT DOCUMENTS 6,896,907 B2   5/2005   Khanuja et al.
7,371,766 B2   5/2008   Snyder et al.

FOREIGN PATENT DOCUMENTS

IN    3040MUM2010 A    1/2011
IN    201821002010 A   12/2018
WO    2019/142062 A2    7/2019

OTHER PUBLICATIONS

Corresponding PCT Application No. PCT/IB2020/051111, International Search Report mailed Jul. 9, 2020.
Corresponding PCT Application No. PCT/IB2020/051111, Written Opinion mailed Jul. 9, 2020.
Corresponding Indian Patent Application No. 201921006145, Office Action dated Jul. 6, 2021. English Translation.
Gurpreet Kaur Randhawa, et al., "Chemotherapeutic Potential of Cow Urine: A Review", Journal of Intercultural Ethnapharmacology, Mar. 7, 2015, pp. 180-186, vol. 4, Issue 2.
Jain, et al., "Efficacy of Cow Urine Therapy on Various Cancer Patients in Mandsaur District, India—A Survey", International Journal of Green Pharmacy, Jan. 2, 2009, pp. 29-36.
Krup, et al., "Pharmacological Activities of Turmeric (*Curcuma longa linn*): A Review", Journal of Homeopathic & Ayurvedic Medicine, 2013, vol. 2, Issue 4.

*Primary Examiner* — Qiuwen Mi
(74) *Attorney, Agent, or Firm* — Cooper Legal Group, LLC

(57) ABSTRACT

The present invention provides a synergistic composition that exhibits an anti-proliferative activity, the composition including: therapeutically effective amount of Turmeric (*Curcuma* spp.); and therapeutically effective amount of Cow urine (Gomutra). The composition comprising a combination of Cow urine and Turmeric extract exhibits unexpected synergistic effect and significantly reduce and/or control the proliferation of cancer cells as compared to Cow urine and Turmeric when used alone.

8 Claims, No Drawings

SYNERGISTIC COMPOSITION WITH ANTI-PROLIFERATIVE ACTIVITY

CROSS-REFERENCE TO RELATED APPLICATIONS

This application is a national stage filing under 35 U.S.C. § 371 of International Application No.: PCT/IB2020/051111, filed on 12 Feb. 2020, which claims priority of India Patent Application No.: 201921006145, filed on 15 Feb. 2019, which is incorporated herein by reference in its entirety.

TECHNICAL FIELD

The present disclosure relates to the compositions that exhibit anti-proliferative activity. Particularly, the present disclosure provides a synergistic composition including a combination of therapeutically effective amount of Turmeric (*Curcuma* Spp.) and therapeutically effective amount of Cow urine (Gomutra) that exhibits anti-proliferative activity.

BACKGROUND

Background description includes information that may be useful in understanding the present invention. It is not an admission that any of the information provided herein is prior art or relevant to the presently claimed invention, or that any publication specifically or implicitly referenced is prior art.

Cancer is a disease characterized by increase in the number of abnormal cells derived from normal tissue/cells, with the cancerous cells typically invading adjacent tissues or metastasizing by spreading through the blood to other regions of the body. Cancer typically progresses through a multistep process that begins with minor pre-neoplastic changes, which may progress to neoplasia, the neoplastic lesions possibly developing an increasing capacity for invasion, growth, metastasis, and heterogencity.

The incidence of cancer continues to climb as the general population ages, as new cancers develop, and as susceptible populations grow. A tremendous demand exists for new methods and compositions that can be used to treat patients with cancer. Current therapy may involve surgery, chemotherapy, hormonal therapy and/or radiation treatment to eradicate neoplastic cells in a patient. Other therapies include biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

Overall, chemotherapy often has many drawbacks. Many chemotherapeutic agents are toxic to healthy cells, and chemotherapy can cause significant and dangerous side effects, including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by a different mechanism from the drugs used in the specific treatment. This phenomenon is referred to as pleiotropic drug or multidrug resistance. Because of such drug resistance, many cancers prove refractory to standard chemotherapeutic treatment protocols.

Significant efforts has been put forward towards finding new and safe NCEs and to device new formulations of the existing and approved drugs to limit the side effects exhibited by these therapeutic agents. However, none of the current approaches/reports seem to satisfy the existing needs.

There is, therefore, a need in the art to develop new composition and/or formulation that exhibits desired therapeutic activity while being substantially devoid of toxic effects/side-effects. The present disclosure satisfies the existing needs, inter alia, others and provides a composition that exhibits synergistic anti-cancer activity.

OBJECTS OF THE INVENTION

An object of the present disclosure is to provide a composition that exhibits desired therapeutic efficacy against cancer and related disorders that satisfies the existing needs, as well as others, and generally overcomes the deficiencies found in the prior art.

Another object of the present disclosure is to provide a composition that exhibits desired therapeutic efficacy against cancer and related disorders while being substantially devoid of side effects.

Another object of the present disclosure is to provide a composition that exhibits desired therapeutic efficacy against cancer and related disorders that is cost effective.

Another object of the present disclosure is to provide a composition that exhibits desired therapeutic efficacy against cancer and related disorders that is easy to manufacture.

Another object of the present disclosure is to provide a process for preparation of a composition that exhibits synergistic anti-proliferative effect.

SUMMARY

The present disclosure relates to the compositions that exhibits anti-proliferative activity. Particularly, the present disclosure provides a synergistic composition including a combination of therapeutically effective amount of Turmeric (*Curcuma* spp.) and therapeutically effective amount of Cow urine (Gomutra) that exhibits anti-proliferative effect.

An aspect of the present disclosure provides a synergistic composition that exhibits an anti-proliferative activity, the composition including: therapeutically effective amount of Turmeric (*Curcuma* spp.); and therapeutically effective amount of Cow urine (Gomutra). In an embodiment, the composition includes an extract of Turmeric (*Curcuma* spp.). In an embodiment, the composition includes comminuted plant part of Turmeric (*Curcuma* spp.). In an embodiment, the composition includes powdered Turmeric (*Curcuma* spp.). In an embodiment, the composition includes Turmeric (*Curcuma* spp.) in an amount ranging from about 1% to about 99% by weight of the composition. In an embodiment, the composition includes Turmeric (*Curcuma* spp.) in an amount ranging from about 0.25% to about 99.75% by weight of the composition. In an embodiment, the composition includes Turmeric (*Curcuma* spp.) in an amount ranging from about 3% to about 97% by weight of the composition. In an embodiment, the composition includes Turmeric (*Curcuma* spp.) in an amount ranging from about 5% to about 95% by weight of the composition. In an embodiment, the composition includes Turmeric (*Curcuma* spp.) in an amount ranging from about 10% to about 90% by weight of the composition. In an embodiment, the composition includes Turmeric (*Curcuma* spp.) in an amount ranging from about 15% to about 85% by weight of the composition. In an embodiment, the composition includes Turmeric (*Curcuma* spp.) in an amount ranging from about 20% to about 80% by weight of the composition. In an embodiment, the composition includes Cow urine (Gomutra) in an amount ranging from about 0.25% to about 99.75% by weight of the composition. In an embodiment, the composition includes Cow urine (Gomutra) in an amount ranging from about 1% to about 99% by weight of the composition. In an embodiment, the composition includes Cow urine (Gomutra) in an amount ranging from about 3% to about 97% by weight of the composition. In an embodiment, the composition includes Cow urine (Gomutra) in an amount ranging from about 5% to about 95% by weight of the composition. In an embodiment, the composition includes Cow urine (Gomutra) in an amount ranging from about 7% to about 93% by weight of the composition. In an embodiment, the composition includes Cow urine (Gomutra) in an amount ranging from about 10% to about 90% by weight of the composition. In an embodiment, the composition includes Cow urine (Gomutra) in an amount ranging from about 15% to about 85% by weight of the composition. In an embodiment, the composition includes Cow urine (Gomutra) in an amount ranging from about 20% to about 80% by weight of the composition. In an embodiment, the composition comprises cow urine (Gomutra) in an amount ranging from 50% to 70% by weight of the composition and Turmeric (*Curcuma* spp.) in an amount ranging from 30% to 50% by weight of the composition. In an embodiment, the composition comprises cow urine (Gomutra) in an amount ranging from 60% to 70% by weight of the composition and Turmeric (*Curcuma* spp.) in an amount ranging from 30% to 40% by weight of the composition. In an embodiment, the composition comprises cow urine (Gomutra) in an amount of 67% by weight of the composition and Turmeric (*Curcuma* spp.) in an amount of 33% by weight of the composition. In an embodiment, the composition further includes pharmaceutically acceptable excipient. In an embodiment, the composition is formulated as a tablet. In an embodiment, the composition further includes therapeutically effective amount of any or a combination of an extract of myrrh, an extract of mustard, an extract of Oregano, an extract of benzoin, an extract of Niouli, an extract of tea tree, an extract of cinnamon, an extract of clove, an extract of basil, an extract of ginger, an extract of lavender, an extract of neem, an extract of chamomile, germanium or analogue thereof. In an embodiment, the composition further includes camphor and bees wax. However, a person skilled in the art would appreciate that any other natural, semi-synthetic or synthetic molecule that can supplement and/or increase the anti-cancer activity of the composition of the instant disclosure can be used in addition to the herbs utilized in the present disclosure. In an embodiment, the composition is formulated into any of a solid composition, a semi-solid composition and a liquid composition. In an embodiment, the composition is formulated into a single unit oral dosage form. In an embodiment, the composition is formulated into a topical formulation. In an embodiment, the composition exhibits anti-proliferative activity against breast cancer. In an embodiment, the cow urine comprises any or a combination of filtered cow urine, unfiltered fresh cow urine, cow urine ark, cow urine distillate and cow urine concoction.

Various objects, features, aspects and advantages of the inventive subject matter will become more apparent from the following detailed description of preferred embodiments, along with the accompanying drawing figures in which like numerals represent like components.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments, on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an." and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms as used herein are shown below. To the extent a term used in a claim is not defined below, it should be given the broadest definition persons in the pertinent art have given that term as reflected in printed publications and issued patents at the time of filing.

As used herein, the term "therapeutically effective amount" denotes an amount of a compound of the present invention effective to yield a desired therapeutic response. For example to prevent cancer or treat the symptoms of cancer in a host or an amount effective to treat cancer. The specific "therapeutically effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical carrier" or "pharmaceutically acceptable excipient" is a pharmaceutically acceptable solvent, suspending agent or vehicle for delivering the anti-cancer agent to the animal or human. The carrier may be liquid or solid and is selected based on the route of administration, as commonly known to a person skilled in the pertinent art.

As used herein, "a subject in need thereof" is a patient, animal, mammal or human, who will benefit from the method of this invention. This patient may be a person genetically disposed to cancer or a patient who is believed to be at risk for developing cancer or a person diagnosed with one or more types of cancer.

As used herein, the term "treatment," "treating," "palliating" and "ameliorating" are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The present disclosure relates generally to the compositions that exhibits anti-proliferative activity. Particularly, the present disclosure provides a synergistic composition including a combination of therapeutically effective amount of Turmeric (*Curcuma* spp.) and therapeutically effective amount of Cow urine (Gomutra) that exhibits anti-proliferative effect.

The present disclosure is based, at least in part, on premise of unexpected discovery that the composition of the present disclosure exhibits surprisingly high anti-proliferative activity on account of synergism between the ingredients/components of the composition viz. Turmeric (*Curcuma* spp.) and Cow urine (Gomutra).

Accordingly, an aspect of the present disclosure provides a synergistic composition that exhibits an anti-proliferative activity, the composition including: therapeutically effective amount of Turmeric (*Curcuma* spp.), and therapeutically effective amount of Cow urine (Gomutra). In an embodiment, the composition includes an extract of Turmeric (*Curcuma* spp.). In an embodiment, the composition includes comminuted plant part of Turmeric (*Curcuma* spp.) In an embodiment, the composition includes powdered Turmeric (*Curcuma* spp.). In an embodiment, the composition includes Turmeric (*Curcuma* spp.) in an amount ranging from about 0.25% to about 99.75% by weight of the composition. In an embodiment, the composition includes Turmeric (*Curcuma* spp.) in an amount ranging from about 1% to about 99% by weight of the composition. In an embodiment, the composition includes Turmeric (*Curcuma* spp.) in an amount ranging from about 3% to about 97% by weight of the composition. In an embodiment, the composition includes Turmeric (*Curcuma* spp) in an amount ranging from about 5% to about 95% by weight of the composition. In an embodiment, the composition includes Turmeric (*Curcuma* spp.) in an amount ranging from about 10% to about 90% by weight of the composition. In an embodiment, the composition includes Turmeric (*Curcuma* spp.) in an amount ranging from about 15% to about 85% by weight of the composition. In an embodiment, the composition includes Turmeric (*Curcuma* spp.) in an amount ranging from about 20% to about 80% by weight of the composition. In an embodiment, the composition includes Cow urine (Gomutra) in an amount ranging from about 0.25% to about 99.75% by weight of the composition. In an embodiment, the composition includes Cow urine (Gomutra) in an amount ranging from about 1% to about 99% by weight of the composition. In an embodiment, the composition includes Cow urine (Gomutra) in an amount ranging from about 3% to about 97% by weight of the composition. In an embodiment, the composition includes Cow urine (Gomutra) in an amount ranging from about 5% to about 95% by weight of the composition. In an embodiment, the composition includes Cow urine (Gomutra) in an amount ranging from about 7% to about 93% by weight of the composition. In an embodiment, the composition includes Cow urine (Gomutra) in an amount ranging from about 10% to about 90% by weight of the composition. In an embodiment, the composition includes Cow urine (Gomutra) in an amount ranging from about 15% to about 85% by weight of the composition. In an embodiment, the composition includes Cow urine (Gomutra) in an amount ranging from about 20% to about 80% by weight of the composition. In an embodiment, the composition comprises cow urine (Gomutra) in an amount ranging from 50% to 70% by weight of the composition and Turmeric (*Curcuma* spp.) in an amount ranging from 30% to 50% by weight of the composition. In an embodiment, the composition comprises cow urine (Gomutra) in an amount ranging from 60% to 70% by weight of the composition and Turmeric (*Curcuma* spp.) in an amount ranging from 30% to 40% by weight of the composition. In an embodiment, the composition comprises cow urine (Gomutra) in an amount of 67% by weight of the composition and Turmeric (*Curcuma* spp.) in an amount of 33% by weight of the composition. In an embodiment, the composition further includes pharmaceutically acceptable excipient. In an embodiment, the composition is formulated as a tablet. In an embodiment, the composition further includes therapeutically effective amount of any or a combination of: an extract of myrrh, an extract of mustard, an extract of Oregano, an extract of benzoin, an extract of Niouli, an extract of tea tree, an extract of cinnamon, an extract of clove, an extract of basil, an extract of ginger, an extract of lavender, an extract of neem, an extract of chamomile, germanium or analogue thereof. In an embodiment, the composition further includes camphor and bees wax. However, a person skilled in the art would appreciate that any other natural, semi-synthetic or synthetic molecule that can supplement and/or increase the anti-cancer activity of the composition of the instant disclosure can be used in addition to the herbs utilized in the present disclosure. In an embodiment, the composition is formulated into any of a solid composition, a semi-solid composition and a liquid composition. In an embodiment, the composition is formulated into a single unit oral dosage form. In an embodiment, the composition is formulated into a topical formulation. In an embodiment, the composition exhibits anti-proliferative activity against breast cancer. In an embodiment, the cow urine comprises any or a combination of filtered cow urine, unfiltered fresh cow urine, cow urine ark, cow urine distillate and cow urine concoction.

In an embodiment, the pharmaceutical formulation for treating cancer cells include, optionally, any or a combination of one or more pharmaceutically acceptable excipients. Non-limiting examples of suitable excipients includes a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents. However, a person skilled in the art would appreciate that any other excipient(s), as known to or appreciated by a person skilled in the art can be utilized to serve its intended purpose in the instant invention, without departing from the scope and the spirit of the present disclosure.

In an embodiment, the excipient can be a binder. Non-limiting example of suitable binders include, starches, pregelatinized starches, gelatin, polyvinylpyrolidone, cellulose, methylcellulose, sodium carboxymethylcellulose, ethylcellulose, polyacrylamides, polyvinvloxoazolidone, polyvinylalcohols. C12-C18 fatty acid alcohol, polyethylene glycol, polyols, saccharides, oligosaccharides, polypeptides, peptides, and combinations thereof. However, a person skilled in the art would appreciate that any other binder(s), as known to or appreciated by a person skilled in the art can be utilized to serve its intended purpose in the instant invention, without departing from the scope and the spirit of the present disclosure.

In an embodiment, the excipient can be a filler. Non-limiting example of suitable fillers include, carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol and combinations thereof. However, a person skilled in the art would appreciate that any other filler(s), as known to or appreciated by a person skilled in the art can be utilized to serve its intended purpose in the instant invention, without departing from the scope and the spirit of the present disclosure.

In an embodiment, the excipient can be a non-effervescent disintegrant. Non-limiting example of suitable non-effervescent disintegrants include, starches (such as corn starch, potato starch, and the like), pregelatinized and modified starches thereof, sweeteners, clays (such as bentonite), micro-crystalline cellulose, alginates, sodium starch glycolate, and gums (such as agar, guar, locust bean, karaya, pecitin, and tragacanth) and combinations thereof. However, a person skilled in the art would appreciate that any other non-effervescent disintegrant(s), as known to or appreciated by a person skilled in the art can be utilized to serve its intended purpose in the instant invention, without departing from the scope and the spirit of the present disclosure.

In an embodiment, the excipient can be an effervescent disintegrant. Non-limiting example of suitable effervescent disintegrants include, sodium bicarbonate in combination with citric acid, and sodium bicarbonate in combination with tartaric acid. However, a person skilled in the art would appreciate that any other effervescent disintegrant(s), as known to or appreciated by a person skilled in the art can be utilized to serve its intended purpose in the instant invention, without departing from the scope and the spirit of the present disclosure.

In an embodiment, the excipient can be a preservative. Non-limiting example of suitable preservatives include, antioxidants (such as alpha-tocopherol or ascorbate) and antimicrobials (such as parabens, chlorobutanol or phenol). In other embodiments, an antioxidant such as butylatedhydroxytoluene (BHT) or butylatedhydroxyanisole (BHA) may be utilized. However, a person skilled in the art would appreciate that any other preservative(s), as known to or appreciated by a person skilled in the art can be utilized to serve its intended purpose in the instant invention, without departing from the scope and the spirit of the present disclosure.

In an embodiment, the excipient can be a diluent. Non-limiting example of suitable diluents includes pharmaceutically acceptable saccharides, such as, sucrose, dextrose, lactose, microcrystalline cellulose, fructose, xylitol, and sorbitol; polyhydric alcohols; starches; pre-manufactured direct compression diluents; and combination thereof. However, a person skilled in the art would appreciate that any other diluent(s), as known to or appreciated by a person skilled in the art can be utilized to serve its intended purpose in the instant invention, without departing from the scope and the spirit of the present disclosure.

In an embodiment, the excipient can be a flavoring agent. Non-limiting example of suitable flavoring agents include, synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot) and combination thereof. However, a person skilled n the art would appreciate that any other flavoring agent(s), as known to or appreciated by a person skilled in the art can be utilized to serve its intended purpose in the instant invention, without departing from the scope and the spirit of the present disclosure.

In an embodiment, the excipient can be a sweetener. Non-limiting example of suitable sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. However, a person skilled in the art would appreciate that any other sweetener(s), as known to or appreciated by a person skilled in the art can be utilized to serve its intended purpose in the instant invention, without departing from the scope and the spirit of the present disclosure. In an embodiment, the excipient can be a lubricant. Non-limiting example of suitable lubricants include magnesium stearate, calcium stearate, zinc stearate, hydrogenated vegetable oils, sterotex, polyoxyethylenemonostearate, talc, polyethyleneglycol, sodium benzoate, sodium lauryl sulfate, magnesium lauryl sulfate, and light mineral oil and combination thereof. However, a person skilled in the art would appreciate that any other lubricant(s), as known to or appreciated by a person skilled in the art can be utilized to serve its intended purpose in the instant invention, without departing from the scope and the spirit of the present disclosure.

In an embodiment, the excipient can be a dispersants. Non-limiting example of suitable dispersants include starch, alginic acid, polyvinylpyrrolidones, guar gum, kaolin, bentonite, purified wood cellulose, sodium starch glycolate, isoamorphous silicate, and microcrystalline cellulose. However, a person skilled in the art would appreciate that any other dispersant(s), as known to or appreciated by a person skilled in the art can be utilized to serve its intended purpose in the instant invention, without departing from the scope and the spirit of the present disclosure.

In an embodiment, the excipient can be an emulsifier. Non-limiting example of suitable emulsifiers include emulsifying wax, cetearyl alcohol, polysorbate 20, and ceteareth 20, Sodium stearoyllactylate, Sodium phosphates, soy lecithin and the likes. However, a person skilled in the art would appreciate that any other emulsifier(s), as known to or appreciated by a person skilled in the art can be utilized to serve its intended purpose in the instant invention, without departing from the scope and the spirit of the present disclosure.

In an embodiment, the pharmaceutical composition can include a coloring agent. Non-limiting example of suitable coloring agents include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment. However, a person skilled in the art would appreciate that any other coloring agent(s), as known to or appreciated by a person skilled in the art can be utilized to serve its intended purpose in the instant invention, without departing from the scope and the spirit of the present disclosure.

In an embodiment, the excipient can be a taste-masking agent. Non-limiting example of suitable taste-masking materials include, cellulose hydroxypropyl ethers (HPC), low-substituted hydroxypropyl ethers (L-HPC), cellulose hydroxypropyl methyl ethers (HPMC), methylcellulose polymers and mixtures thereof; polyvinyl alcohol (PVA), hydroxyethylcelluloses, carboxymethylcelluloses and salts thereof, polyvinyl alcohol and polyethylene glycol co-polymers, monoglycerides or triglycerides, polyethylene glycols, acrylic polymers, mixtures of acrylic polymers with cellulose ethers, cellulose acetate phthalate, and combinations thereof. However, a person skilled in the art would appreciate that any other taste-masking agent(s), as known to or appreciated by a person skilled in the art can be utilized to serve its intended purpose in the instant invention, without departing from the scope and the spirit of the present disclosure.

In an embodiment, the excipient can be a pH modifier. Non-limiting example of suitable pH modifier include sodium carbonate or sodium bicarbonate. However, a person skilled in the art would appreciate that any other pH modifier (s), as known to or appreciated by a person skilled in the art can be utilized to serve its intended purpose in the instant invention, without departing from the scope and the spirit of the present disclosure.

In an embodiment, the weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein can be manufactured in one or several dosage forms. In an embodiment, pharmaceutical dosage form is selected from any or a combination of tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules, lozenges, a sachet, a sprinkle, a reconstitutable powder or shake, a troche, pellets such as sublingual or buccal pellets, granules, liquids for oral or parenteral administration, suspensions, emulsions, semisolids, or gels. However, any or a combination of pharmaceutical dosage form(s), as known to or appreciated by a person skilled in the art, can be utilized to serve its intended purpose, as laid in the present disclosure, without departing from the scope and spirit of the present invention.

In an embodiment, the composition is formulated as a tablet. In an embodiment, the tablet formulation includes Turmeric (*Curcuma* spp.) in an amount ranging from about 0.25% to about 99.75% by weight of the composition and Cow urine (Gomutra) in an amount ranging from about 0.25% to about 99.75% by weight of the composition. In an embodiment, the tablet formulation includes Turmeric (*Curcuma* spp.) in an amount ranging from about 1% to about 99% by weight of the composition and Cow urine (Gomutra) in an amount ranging from about 1% to about 99% by weight of the composition.

In an embodiment, the composition is formulated as a tablet. In an embodiment, the tablet formulation includes Turmeric (*Curcuma* spp.) in an amount ranging from about 3% to about 97% by weight of the composition and Cow urine (Gomutra) in an amount ranging from about 3% to about 97% by weight of the composition.

In an embodiment, the composition is formulated as a tablet. In an embodiment, the tablet formulation includes Turmeric (*Curcuma* spp.) in an amount ranging from about 5% to about 95% by weight of the composition and Cow urine (Gomutra) in an amount ranging from about 5% to about 95% by weight of the composition.

In an embodiment, the composition is formulated as a tablet. In an embodiment, the tablet formulation includes Turmeric (*Curcuma* spp.) in an amount ranging from about 7% to about 93% by weight of the composition and Cow urine (Gomutra) in an amount ranging from about 7% to about 93% by weight of the composition.

In an embodiment, the composition is formulated as a tablet. In an embodiment, the tablet formulation includes Turmeric (*Curcuma* spp.) in an amount ranging from about 10% to about 90% by weight of the composition and Cow urine (Gomutra) in an amount ranging from about 10% to about 90% by weight of the composition.

In an embodiment, the composition is formulated as a tablet. In an embodiment, the tablet formulation includes Turmeric (*Curcuma* spp.) in an amount ranging from about 15% to about 85% by weight of the composition and Cow urine (Gomutra) in an amount ranging from about 15% to about 85% by weight of the composition.

In an embodiment, the tablet formulation includes Turmeric (*Curcuma* spp.) in an amount ranging from about 20% to about 80% by weight of the composition and Cow urine (Gomutra) in an amount ranging from about 20% to about 80% by weight of the composition.

In an embodiment, the tablet formulation comprises cow urine (Gomutra) in an amount ranging from 50% to 70% by weight of the formulation and Turmeric (*Curcuma* spp.) in an amount ranging from 30% to 50% by weight of the formulation.

In an embodiment, the tablet formulation comprises cow urine (Gomutra) in an amount ranging from 60% to 70% by weight of the formulation and Turmeric (*Curcuma* spp.) in an amount ranging from 30% to 40% by weight of the formulation.

In an embodiment, the tablet formulation comprises cow urine (Gomutra) in an amount of 67% by weight of the formulation and Turmeric (*Curcuma* spp.) in an amount of 33% by weight of the formulation.

In an embodiment, the composition is present in the form of a topical formulation. In an embodiment, the topical formulation includes Turmeric (*Curcuma* spp.) in an amount ranging from about 0.25% to about 99.75% by weight of the composition and Cow urine (Gomutra) in an amount ranging from about 0.25% to about 99.75% by weight of the composition. In an embodiment, the topical formulation includes Turmeric (*Curcuma* spp.) in an amount ranging from about 1% to about 99% by weight of the composition and Cow urine (Gomutra) in an amount ranging from about 1% to about 99% by weight of the composition.

In an embodiment, the topical formulation includes Turmeric (*Curcuma* spp.) in an amount ranging from about 3% to about 97% by weight of the composition and Cow urine (Gomutra) in an amount ranging from about 3% to about 97% by weight of the composition.

In an embodiment, the topical formulation includes Turmeric (*Curcuma* spp.) in an amount ranging from about 5% to about 95% by weight of the composition and Cow urine (Gomutra) in an amount ranging from about 5% to about 95% by weight of the composition.

In an embodiment, the topical formulation includes Turmeric (*Curcuma* spp.) in an amount ranging from about 7% to about 93% by weight of the composition and Cow urine (Gomutra) in an amount ranging from about 7% to about 93% by weight of the composition.

In an embodiment, the topical formulation includes Turmeric (*Curcuma* spp.) in an amount ranging from about 10% to about 90% by weight of the composition and Cow urine (Gomutra) in an amount ranging from about 10% to about 90% by weight of the composition.

In an embodiment, the topical formulation includes Turmeric (*Curcuma* spp.) in an amount ranging from about 15% to about 85% by weight of the composition and Cow urine (Gomutra) in an amount ranging from about 15% to about 85% by weight of the composition.

In an embodiment, the topical formulation includes Turmeric (*Curcuma* spp.) in an amount ranging from about 20% to about 80% by weight of the composition and Cow urine (Gomutra) in an amount ranging from about 20% to about 80% by weight of the composition.

In an embodiment, the topical formulation comprises cow urine (Gomutra) in an amount ranging from 50% to 70% by weight of the formulation and Turmeric (*Curcuma* spp.) in an amount ranging from 30% to 50% by weight of the formulation.

In an embodiment, the topical formulation comprises cow urine (Gomutra) in an amount ranging from 60% to 70% by weight of the formulation and Turmeric (*Curcuma* spp.) in an amount ranging from 30% to 40% by weight of the formulation.

In an embodiment, the topical formulation comprises cow urine (Gomutra) in an amount of 67% by weight of the formulation and Turmeric (*Curcuma* spp.) in an amount of 33% by weight of the formulation.

The present invention provides a method of treating cancer comprising: administering to a subject in need thereof, a pharmaceutically effective amount of a synergistic composition, wherein the composition comprises therapeutically effective amount of Turmeric (*Curcuma* spp.); and therapeutically effective amount of Cow urine (Gomutra).

In addition, the present invention provides a pharmaceutical formulation for treating cancer cells, wherein the pharmaceutical formulation comprises: a physiologically effective amount of a composition in a pharmaceutical carrier sufficient to inhibit the growth of cancer cells, wherein the composition comprises therapeutically effective amount of Turmeric (*Curcuma* spp.); and therapeutically effective amount of Cow urine (Gomutra).

In an embodiment, the pharmaceutical formulation for treating cancer cells is present in form of a tablet. In an embodiment, the tablet formulation for treating cancer cells includes Turmeric (*Curcuma* spp.) in an amount ranging from about 1% to about 99% by weight of the composition and Cow urine (Gomutra) in an amount ranging from about 1% to about 99% by weight of the composition. In an embodiment, the tablet formulation further includes pharmaceutically acceptable excipient.

In an embodiment, the pharmaceutical formulation for treating cancer cells is present in form of a topical formulation. In an embodiment, the topical formulation includes Turmeric (*Curcuma* spp.) in an amount ranging from about 1% to about 99% by weight of the composition and Cow urine (Gomutra) in an amount ranging from about 1% to about 99% by weight of the composition. In an embodiment, the topical formulation further includes pharmaceutically acceptable excipient.

The present invention provides a pharmaceutical formulation for treating one or more symptom of cancer, wherein the composition comprises therapeutically effective amount of Turmeric (*Curcuma* spp.); and therapeutically effective amount of Cow urine (Gomutra) to ameliorate one or more symptoms of the cancer.

The present invention also provides a composition for reducing the number of cancer cells, wherein the composition comprises therapeutically effective amount of an extract of Turmeric (*Curcuma* spp.); and therapeutically effective amount of Cow urine (Gomutra) to reduce the number of the one or more cancer cells.

In an embodiment, the pharmaceutical formulation for reducing the number of cancer cells is present in form of a tablet. In an embodiment, the tablet formulation for reducing the number of cancer cells includes Turmeric (*Curcuma* spp.) in an amount ranging from about 1% to about 99% by weight of the composition and Cow urine (Gomutra) in an amount ranging from about 1% to about 99% by weight of the composition. In an embodiment, the tablet formulation further includes pharmaceutically acceptable excipient.

In an embodiment, the pharmaceutical formulation for reducing the number of cancer cells is present in form of a topical formulation. In an embodiment, the topical formulation includes Turmeric (*Curcuma* spp.) in an amount ranging from about 1% to about 99% by weight of the composition and Cow urine (Gomutra) in an amount ranging from about 1% to about 99% by weight of the composition. In an embodiment, the topical formulation further includes pharmaceutically acceptable excipient.

In an embodiment, the pharmaceutical formulation can be advantageously utilized for the treatment of anemia, epilepsy, skin diseases and related disorders. In an embodiment, the pharmaceutical formulation can also be used as health supplement to increase mineral content of the body and to provide bactericidal and detoxification effect.

The present invention provides a method for reducing the number of cancer cells in a mammal by identifying a mammal having one or more cancer cells; administering a therapeutically effective dose of the formulation to the mammal to reduce the number of cancer cells, wherein the formulation comprises therapeutically effective amount of an extract of Turmeric (*Curcuma* spp.) and therapeutically effective amount of Cow urine (Gomutra); and monitoring the number of cancer cells in the mammal.

Specifically, the present invention utilizes *Curcuma longa*, commonly found throughout the Indian terrain. Rhizomes or underground stem and roots of Turmeric or the crushed powder of its dried form can be used. Preferably. Turmeric rhizomes, either fresh or dried, are used to subserve its intended purpose, as laid down in embodiments of the present disclosure. Also found to be particularly suitable is extract of the rhizome or underground stem of Turmeric (*Curcuma longa*). Any extraction method as known to a person skilled in the art can be utilized for the instant invention. In an embodiment, the present invention utilizes extract (e.g., ethanol extract) from Turmericrhizomes that show antitumor activity in vitro. Any commercially available extract can also be used. Extracts are usually available in concentrated liquid or dried powder form. However, extract prepared by any other method for isolation and extraction of active compounds, as known to or appreciated by a person skilled in the art, for example maceration, soxhlet extraction, microwave-assisted extraction (MAE), ultrasound-assisted extraction (UAE), supercritical fluid extraction (SFE) and the likes can be used to serve its intended purpose, as laid down in the present disclosure without departing from the scope and spirit of the present invention. Also found to be suitable, for the present compositions of the present disclosure, is turmeric oils such as essential oil(s) of turmeric that includes active constituents of turmeric. Any method known to or appreciated by a person skilled in the art can be used for extraction of essential oils from the turmeric.

In the present disclosure, to obtain bioactive compounds with higher extraction efficiencies, supercritical fluid extraction method was used and the anticancer activity of supercritical extract was examined. Supercritical fluid extraction with carbon dioxide allows the isolation of compounds minimizing thermal and chemical degradation. The relatively low temperature of the process and the stability of CO2 allow most compounds to be extracted with little damage or denaturing. The extraction process facilitates collection of volatile oils from the processing material. Volatile oils reduce acute and chronic inflammation and more importantly help in absorption of other compounds in humans. Extracts obtained with application of supercritical fluid extraction am very stable and can be used directly in diet supplementation.

The present invention typically utilizes Cow Urine (Gomutra) that belongs to the animal origin with numerable therapeutic value. Specifically, the present invention utilizes Cow Urine (Gomutra) commonly known as Gomutra. Fresh urine should be filtered before use. Cow urine is usually available in liquid form. The term "Cow urine" as used in various embodiments of the present disclosure denotes Cow urine, either fresh or treated or prepared in any form such as filtered or unfiltered fresh cow urine, cow urine ark, cow urine distillate, cow urine concoction and the likes, as known to or appreciated by a person skilled in the pertinent art and the same can be used for realizing the advantageous compositions and formulations of the present disclosure without departing from the scope and spirit of the present disclosure.

EXAMPLES

The present disclosure is further explained in the form of an example. However, it is to be understood that the example is merely illustrative and is not to be taken as limitations upon the scope of the invention. Various changes and modifications to the disclosed embodiments will be apparent to those skilled in the art. Such changes and modifications may be made without departing from the scope of the invention.

The synergistic herbal compositions including Cow Urine (Gomutra) and Turmeric (*Curcuma longa*) were evaluated for its ability to reduce and/or control the growth of cancerous cells in Breast Cancer Cell lines (MCF-7). MTT assay was conducted for measuring % inhibition of breast cancer cells by the compositions (i.e. observation of proliferation of breast cancer cell line, MCF-7).

MTT Assay

Principle: reduction of tetrazolium salts is now widely accepted as a reliable way to examine cell proliferation. Yellow colored MTT (3-(4,5-dimethylthiazolyl-2)-2,5-diphenyltetrazolium bromide) is reduced by metabolically active cells, in part by the action of dehydrogenase enzymes, to generate reducing equivalents such as NADH and NADPH. The resulting intracellular purple formazan can be solubilized and quantified by spectrophotometric means.

In order to carry out MTT Assay, MCF 7 cells were revived and were passaged twice before using for the MTT assay to test the samples. The cell line was maintained continuously till the end of the assay. Ethanol and/or water was used as solvent for preparing the compositions of requisite concentration. Dulbecco's Modified Eagle's Medium (DMEM) (product no. 12-604Q from Lonza India Private Limited) was used as control. Cell count and viability were checked. If viability is above 95% then 5000 cells were seeded per well in sterile 96 well plate, in triplicate for every concentration of each test sample (compositions 1-3 enumerated in Table 1). 10 µl of each of the samples were added per well.

Assay Protocol

Firstly. MCF 7 cells were seeded in 96 well plates at a concentration of 5000 cells/well. Assay included blank wells containing DMEM only, control wells containing DMEM and cells, and test wells containing cells treated with sample/composition. Cell line was then treated with test samples/compositions for 48 hrs. in triplicate. 10 µl of MTT reagent (5 mg/ml) per well was added and incubated for 4 hrs. at 37° C., 5% C02. After incubation. 100 µl of 10% SDS was added per well. After 30 min of further incubation at 37° C., O.D. was read at 570 nm. Percentage Inhibition was calculated by using following formula:

% Inhibition=100−[(O.D. of test/O.D. of control)×100]

Table 1 herein below provides details of compositions used for evaluating the anti-proliferative activity.

TABLE 1

Compositions for evaluation of anti-proliferative activity

| Composition No. | Extract of Turmeric (Curcuma longa) (% v/v) | Cow Urine Ark (% v/v) | Mixture of Cow Urine + Turmeric (% v/v) in a ratio of 67:33 |
|---|---|---|---|
| 1 | 4% | — | — |
| 2 | — | 4% | — |
| 3 | — | — | 4% |

Table 2 below provides effect of compositions (as provided in Table 1 hereinabove) on the growth of cancerous cells in Breast Cancer Cell lines (MCF-7).

TABLE 2

Evaluation of effect of compositions on the growth of cancerous cells in Breast Cancer Cell lines

| Composition No. | % Control Growth |
|---|---|
| 1 (Turmeric extract) | −442 |
| 2 (Cow urine Ark) | 64 |
| 3 (Mix of Turmericextract and Cow Urine Ark) | 73 |

Based on the experiments carried out and as provided hereinabove, it could be concluded that the combination of Cow urine (Cow urine ark) and Turmeric extract (in 67:33 volume ratio) significantly controls the growth of cancerous Human Breast Cancer Cell Line compared to Cow urine Ark and extract of Turmeric (*Curcuma* spp.) when used alone. The composition was found to possess potent anti-proliferative activity.

Advantages of the Invention

The present disclosure provides a composition that exhibits desired therapeutic efficacy against cancer and related disorders that satisfies the existing needs, as well as others, and generally overcomes the deficiencies found in the prior art.

The present disclosure provides a composition that exhibits desired therapeutic efficacy against cancer and related disorders while being substantially devoid of side effects.

The present disclosure provides a composition that exhibits desired therapeutic efficacy against cancer and related disorders that is cost effective.

The present disclosure provides a composition that exhibits desired therapeutic efficacy against cancer and related disorders that is easy to manufacture and can be scaled up for industrial production.

The present disclosure provides a process for preparation of a composition that exhibits synergistic anti-proliferative effect.

I claim:

1. A synergistic herbal composition that exhibits an anti-proliferative activity, the synergistic herbal composition comprising:
   a therapeutically effective amount of cow urine; and
   a therapeutically effective amount of Turmeric, wherein the synergistic herbal composition comprises the cow urine in an amount ranging from about 67% to about 99% by weight of the synergistic herbal composition and wherein the synergistic herbal composition comprises the Turmeric in an amount ranging from about 1% to about 33% by weight of the synergistic herbal composition.

2. The synergistic herbal composition as claimed in claim 1, wherein the synergistic herbal composition comprises any of extract of the Turmeric and powdered Turmeric.

3. The synergistic herbal composition as claimed in claim 1, wherein the cow urine comprises any or a combination of filtered cow urine, unfiltered fresh cow urine, cow urine ark, cow urine distillate and cow urine concoction.

4. The synergistic herbal composition as claimed in claim 1, wherein the synergistic herbal composition comprises the cow urine in an amount of about 99% by weight of the synergistic herbal composition and the Turmeric in an amount of about 1% by weight of the synergistic herbal composition.

5. The synergistic herbal composition as claimed in claim 1, wherein the synergistic herbal composition comprises the cow urine and the Turmeric in a ratio range from 67:33 to 99:1 respectively.

6. The synergistic herbal composition as claimed in claim 1, wherein the synergistic herbal composition comprises the cow urine in an amount of 67% by weight of the synergistic herbal composition and the Turmeric in an amount of 33% by weight of the synergistic herbal composition.

7. The synergistic herbal composition as claimed in claim 1, wherein the synergistic herbal composition is formulated into any of a solid composition, a semi-solid composition and a liquid composition.

8. The synergistic herbal composition as claimed in claim 1, wherein the synergistic herbal composition is formulated into any of an oral dosage formulation and a topical formulation.

* * * * *